United States Patent [19]
Kramer et al.

[11] Patent Number: 5,892,092
[45] Date of Patent: Apr. 6, 1999

[54] PREPARATION OF ALIPHATIC, UNSATURATED NITRILES

[75] Inventors: Andreas Kramer, Freinsheim; Wolfgang Siegel, Limburgerhof; Michael Henningsen, Frankenthal; Georg Heinrich Grosch, Bad Dürkheim, all of Germany

[73] Assignee: BASF Aktiengesellschaft, Ludwigshafen, Germany

[21] Appl. No.: 144,478

[22] Filed: Aug. 31, 1998

[30]    Foreign Application Priority Data

Sep. 4, 1997 [DE] Germany .................. 197 38 576.1

[51] Int. Cl.$^6$ ................................................ C07C 253/00
[52] U.S. Cl. ................................................................ 558/314
[58] Field of Search ................................................ 558/314

[56]    References Cited

U.S. PATENT DOCUMENTS 5,514,830   5/1996   Oku et al. ............................... 558/314

FOREIGN PATENT DOCUMENTS

WO 93/02046   2/1993   WIPO .

OTHER PUBLICATIONS

Alexander J. Fatiadi, "Preparation and Synthetic Applications of Cyano Compounds", the Chemistry of Functional Groups, Supplement C, Part 2, 1983, pp. 1057–1303.

M.N. Rao "A New Method for the Conversion of Aldoximes into Nitriles with Zeolites", Org. Prep. Proceed. Int., vol. 21, No. 2 (1989), pp. 230–232.

Houben–Weyl, "Methoden Der Organischen Chemie", vol. 8 pp. 325–330.

H.M. Meshram, "Dehydration of Alixoimes to Nitriles with Clay", Indian Institute of Chemical Technology, Organic Chemistry Division 1, Synthesis, Oct. 1992, pp. 943–944.

Orazio Attanasi, et al., "Effect of Metal Ions in Organic Synthesis; XVII, Mild, Easy, and High–Yield Conversion of Aldoximes into Nitriles Under Copper (II) Acetate–Catalysis", Synthesis Communications, Sep. 1983, pp. 741–742.

H.M. Sampath Kumar, et al., "Microwave Promoted Rapid Dehydration of Aldoximes to Nitriles on a Solid Support", Organic Division–I, Indian Institute of Chemical Technology, Synthetic Communications, 27(8), (1997), pp. 1327–1333.

*Primary Examiner*—Johann Richter
*Assistant Examiner*—Joseph Murray
*Attorney, Agent, or Firm*—Oblon, Spivak, McClelland, Maier & Neustadt, P.C.

[57]    ABSTRACT

A process for preparing unsaturated nitriles of the formula I

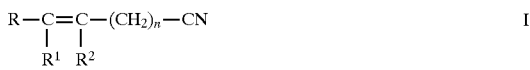

where R, $R^1$ and $R^2$ are each independently of one another alkyl or alkenyl each having 1–20 carbon atoms or cycloalkyl or cycloalkenyl each having 3–12 carbon atoms and any two of the radicals R, $R^1$ and $R^2$ may be part of a saturated or unsaturated ring and $R^1$ and $R^2$ may also be hydrogen and n is 0 or 1–20, by dehydration of oximes of the formula II

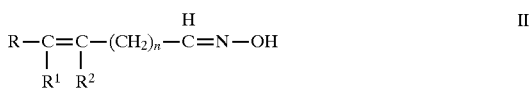

where R, $R^1$, $R^2$ and n are as defined above, comprises dehydrating in the gas or liquid phase at from 150° to 300° C. over a heterogeneous catalyst consisting of an oxidic, carbidic or nitridic support doped with basic oxides and/or hydroxides or compounds which are converted into said oxides or hydroxides under the reaction conditions, or of said basic oxides.

10 Claims, No Drawings

PREPARATION OF ALIPHATIC, UNSATURATED NITRILES

The present invention relates to the preparation of aliphatic, unsaturated nitriles from unsaturated aldoximes by catalytic dehydration in the gas or liquid phase over oxidic, carbidic or nitridic supported catalysts doped with metal oxide or hydroxide bases or over unsupported basic metal oxide catalysts.

There is extensive technical literature relating to the dehydration of aldoximes to give nitriles. A summary of several methods utilizing various reagents is given by A. J. Fatiadi in The Chemistry of Triple Bonded Functional Groups, Supplement D, Part 2, 1057–1303, S. Patai and Z. Rappoport, eds. John-Wiley New York, 1983.

Of particular interest is a recent method of dehydrating citral oxime (3,7-dimethylocta-2,6-dienal oxime) using potassium hydroxide in toluene with removal of water, as described in WO 9302046-A1. However, the disadvantage of this method is that it is less suitable for large scale industrial operation, where processes over heterogeneous catalysts are preferred.

However, dehydrations described to date over heterogeneous catalysts, i.e. customarily in the gas phase, are not yet satisfactory.

The gas phase dehydration of aromatic and aliphatic aldoximes over CsX zeolites described by M. N. Rao et al. in Org. Prep. Proced. Int. 21 (1989) 230–232 requires high temperatures of more than 300° C., for example.

Furthermore, the dehydration of oximes to give nitrites over aluminum or thorium oxides at high temperatures, i.e. more than 340° C., is reviewed in Houben-Weyl, Vol. 8 p. 326 ff.

To avoid these high temperatures, it was then suggested by H. M. Meshram in Synthesis (1992), 943–944 to use montmorillonite KSF, a clay having acidic sites, as a catalyst for the gas phase dehydration of aromatic or saturated aliphatic aldoximes. With this catalyst, the reaction proceeds at lower temperatures, but this process is rendered economically unattractive owing to its insufficient space-time yield.

It is an object of the present invention to provide a process which makes it possible to dehydrate unsaturated aldoximes over heterogeneous catalysts at relatively low temperatures, with short residence times and in good yields.

We have found that this object is achieved by a process for preparing unsaturated nitriles of the formula I

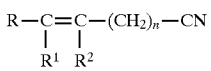    I where R, $R^1$ and $R^2$ are each independently of one another alkyl or alkenyl each having 1–20 carbon atoms or cycloalkyl or cycloalkenyl each having 3–12 carbon atoms and any 2 of the radicals R, $R^1$ and $R^2$ may be part of a saturated or unsaturated ring and $R^1$ and $R^2$ may also be hydrogen and n is 0 or 1–20, in particular 0 or 1–7, by dehydration of oximes of the formula II

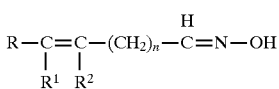    II where R, $R^1$, $R^2$ and n are as defined above, which comprises dehydrating in the gas or liquid phase at from 150° to 300° C. over a heterogeneous catalyst consisting of an oxidic, carbidic or nitridic support doped with basic oxides and/or hydroxides or compounds which are converted into said oxides or hydroxides under the reaction conditions, or of said basic oxides.

Suitable starting materials of formula II are especially compounds where n is 0 or 1–7. Examples of these include angelica oxime, aleprine oxime, α,β-apocitronellal oxime, bergamotene oxime, pyroterebine oxime, campholene oxime, citronellal oxime, citral oxime, chrysantheme oxime, cyclocitral oxime, cyclolavandulal oxime, faranal oxime, farnesal oxime, isolauranal oxime, ikema oxime, myrthenal oxime, phellandrine oxime, safranal oxime and sorbinal oxime.

Preference is given to using compounds of formula I where n is 0.

Specific examples include angelica oxime, bergamotene oxime, cyclolavandulal oxime, citral oxime, farnesal oxime, ikema oxime, isolauranal oxime, phellandrine oxime and sorbinal oxime. In particular, citral oxime is used to give geranonitrile.

Suitable catalysts are generally supported catalysts doped with basic metal oxides or hydroxides. The term doping as used herein means not only the application of the metal oxides or hydroxides, but also ion exchange for, for example, alkali metal or alkaline earth metal ions when support materials are used which are suitable for ion exchange.

As is common practice in most cases, the supports are oxidic, carbidic or nitridic in nature. However, preferred supports are metal oxides of metals of groups Ib to VIIb, VIII and IIIa to Va, in particular IIIb to VIIb, VIII, IIIa and IVa and mixtures thereof.

It is not critical whether the metal oxides are crystalline or amorphous, as determined by X-ray crystallography.

Particular examples are aluminum oxide, silicon dioxide, titanium dioxide and zirconium dioxide in any modification. The carriers generally have a BET surface area of from 0.1 to 500, preferably from 1 to 400, $m^2/g$.

To develop dehydration activity in the range below 300° C., the catalyst supports must be doped with basic metal oxides or hydroxides or metal compounds which form said metal oxides or hydroxides under the reaction conditions.

These metal ions for doping the oxidic materials are selected from groups Ia, IIa to VIII and IIb to Vb, in particular IIb or IIIb, and from the group of the lanthanides consisting of La, Ce, Pr, Nd, Sm, Eu, Gd, Tb, Dy, Ho, Er, Tm, Yb, Lu and mixtures thereof. Preference is given to metal ions of group Ia consisting of Li, Na, K, Rb, Cs and group IIa consisting of Be, Mg, Ca, Sr, Ba. The basic oxide/hydroxide content, based on the catalyst and calculated as oxides, is in the range of 0.1–50% by weight, preferably 0.2–40% by weight, particularly preferably 0.3–30% by weight, especially 1–10% by weight.

The oxidic base materials may be doped by processes known per se, such as impregnation or ion exchange. Following the doping procedure, the catalysts are usually dried and then calcined. The calcination temperature is usually in the range from 150° to 800° C., preferably from 150° to 700° C., particularly preferably from 300° to 650° C.

The dehydration of the unsaturated aldoximes to give the corresponding nitriles is generally carried out batchwise or continuously at from 0.5 to 5 bar and from 150° to 300° C., preferably from 200° to 250° C., particular preference being given to continuous operation. In the continuous process, the aldoximes may be reacted over a fixed bed in the gas or liquid phase or over a fluidized bed in the gas phase.

The reaction of the present invention may be carried out with or without solvents.

Solvents used for the dehydration over a fixed catalyst in the gas phase are especially apolar solvents which are vaporous under the reaction conditions. Examples of suitable solvents are hydrocarbons having up to 12 carbon atoms, such as hexane, heptane or octane.

Suitable solvents for reaction in the liquid phase are solvents which are liquid under the reaction temperatures. These include, in particular, relatively high-boiling hydrocarbons such as paraffin oils and white oils boiling at a temperature of, for example, more than 300° C.

Polar medium- and high-boiling solvents which may be removed from the product by distillation, such as N-methylpyrrolidone, N-methylmorpholine, dimethylpropyleneurea or dimethylethyleneurea, may also be used.

The unsaturated nitrites of the formula II to be produced according to the present invention are obtained in excellent space-time yield with short residence times in the reactor and very good selectivities at good conversions.

EXAMPLES

General procedure

Citral oxime was dehydrated in a laboratory scale gas phase apparatus under the following standard conditions:

Pure citral oxime (E,Z mixture) or a 1:1 solution of citral oxime in N-methylpyrrolidone or n-hexane was fed from a 100 ml dropping funnel into the preheating zone of the gas phase reactor (total length: 500 mm, divided into 200 mm preheating section, 300 ml reaction zone, diameter: 30 mm) at a rate of 13–26 ml/h using a metering pump. The reactor was heated by means of a two-part electrically heated quartz oven. The preheating section was heated to about 210° C. at 500 W, and the reaction zone was heated to 250° C. at 1000 W. The temperature was controlled and monitored by Pt 100 thermocouples in a sheath having a diameter of 6.5 mm located in the longitudinal axis of the reactor. The reaction mixture was reacted over 100 ml of catalyst (extrudates) under an adjustable stream of nitrogen (5–20 l/h, as measured by a rotameter). The gaseous reaction effluent was condensed in an energy ball condenser with a downstream $CO_2$ condenser and collected in a receiver. The reaction effluents were distilled to isolate the geranonitrile.

The results obtained by varying the catalyst and the temperature are given in Tables 1 and 2, respectively.

TABLE 1

| Example | Composition | Solvent | Temperature [°C] | Residence time [sec] | Conversion [%] | Selectivity [%] |
|---|---|---|---|---|---|---|
| 1 | 1% of $Na_2O$ on $Al_2O_3$ (D10-10) | N-methylpyrrolidone | 250 | 16 | >99 | 94 |
| 2a | 2% of $K_2O$ on $Al_2O_3$(Plural ®) | N-methylpyrrolidone | 250 | 28 | >99 | 92 |
| 2b | | n-hexane | 260 | 16 | >99 | 92 |
| 2c | | none | 260 | 16 | >99 | 90 |
| 3a | 2% of $K_2O$ on $TiO_2$ | N-methylpyrrolidone | 250 | 16 | >99 | 91 |
| 3b | | none | 250 | 16 | >99 | 87 |
| 4a | 10% of $Na_2O$ on $SiO_2$ | n-hexane | 250 | 30 | 96 | 92 |
| 4b | | none | 300 | 14 | 94 | 90 |
| 5a | 10% of BaO on $SiO_2$ | n-hexane | 260 | 28 | >99 | 92 |
| 5b | | none | 260 | 8.4 | >99 | 89 |
| 6 | 5% of BaO on $ZrO_2$ | n-hexane none | 255 | 28 | >99 | 86.5 |
| 7 (Comparative) | Quartz rings | n-hexane | 340 | 15 | <4 | — |
| 8 (Comparative) | α-$Al_2O_3$ | n-hexane | 300 | 20 | 79 | 76 |

TABLE 2

| Example | Temperature [°C] | Residence time [sec] | Selectivity [%] |
|---|---|---|---|
| 1a | 250 | 16 | 92 |
| 1b | 300 | 15 | 90 |

TABLE 2-continued

| Example | Temperature [°C] | Residence time [sec] | Selectivity [%] |
|---|---|---|---|
| 1c | 350 | 14 | 72 |
| 1d | 400 | 13 | 32 |

Example 9 (Dehydration in the liquid phase)

A mixture of 10% by weight citral oxime in paraffin oil was reacted over a catalyst (5% of BaO on $ZrO_2$) under atmospheric pressure in an apparatus as described in Example 1. The preheater temperature was 150°–220° C, and the reactor temperature was 220° C. A feed rate of 239 ml/h gave a conversion of more than 98% at a space velocity of 0.95 kg/l×h. Geranonitrile was separated from the reaction mixture leaving the reactor in a wiping-blade evaporator. The nitrile, which may be further purified by distillation, was obtained in a yield of more than 90%.

We claim:

1. A process for preparing unsaturated nitriles of the formula I

where R, $R^1$ and $R^2$ are each independently of one another alkyl or alkenyl each having 1–20 carbon atoms or cycloalkyl or cycloalkenyl each having 3–12 carbon atoms and any two of the radicals R, $R^1$ and $R^2$ may be part of a saturated or unsaturated ring and $R^1$ and $R^2$ may also be hydrogen and n is 0 or 1–20, by dehydration of oximes of the formula II

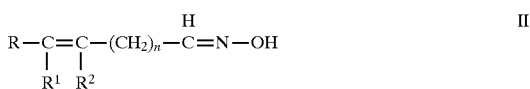

where R, $R^1$, $R^2$ and n are as defined above, which comprises dehydrating in the gas or liquid phase at from 150° to 300° C. over a heterogeneous catalyst consisting of an oxidic, carbidic or nitridic support doped with basic oxides and/or hydroxides or compounds which are converted into said oxides or hydroxides under the reaction conditions, or of said basic oxides.

2. A process as claimed in claim 1, wherein the catalyst used comprises a metal oxide of an element of groups Ib to VIIb and VIII or IIIa to Va of the Periodic Table of the Elements or mixtures thereof as support doped with 0.1–50% by weight, based on the catalyst and calculated as oxides, of basic oxides or hydroxides or compounds of elements of groups Ia, IIa, IIb to Vb and/or lanthanide elements which form basic oxides or hydroxides under the reaction conditions.

3. A process as claimed in claim 1, wherein the catalyst used comprises a metal oxide of an element of groups IIb to VIIb or VIII or IIIa to IVa of the Periodic Table of the Elements or mixtures thereof as support doped with 0.2–40% by weight, based on the catalyst and calculated as oxides, of alkali metal or alkaline earth metal oxides or hydroxides or compounds which are converted into said oxides or hydroxides under the reaction conditions.

4. A process as claimed in claim 1, wherein the catalyst used comprises 0.3–30% by weight, based on the catalyst and calculated as oxides, of alkali metal or alkaline earth metal oxides or hydroxides on an oxide support selected from the group consisting of aluminum oxide, silicon dioxide, titanium dioxide and zirconium dioxide.

5. A process as claimed in claim 1, wherein the catalyst used comprises 1–10% by weight, calculated as oxides, of alkali metal or alkaline earth metal oxides or hydroxides.

6. A process as claimed in claim 1, wherein the oxidic catalyst used is a shaped catalyst selected from the group consisting of aluminum oxide, silicon dioxide, titanium dioxide and zirconium dioxide which has been impregnated with a solution of an alkaline alkali metal or alkaline earth metal compound and calcined at from 300° to 650° C.

7. A process as claimed in claim 1, wherein the dehydration is carried out in the gas phase in the presence of a solvent which is vaporous under the reaction conditions.

8. A process as claimed in claim 1, wherein the dehydration is carried out in the liquid phase in the presence of a solvent which is liquid under the reaction conditions.

9. A process as claimed in claim 1, wherein the reaction is carried out at from 200° to 250° C. and from 0.5 to 5 bar.

10. A process as claimed in claim 1, wherein citral oxime is dehydrated to give geranonitrile.

* * * * *